(12) United States Patent
Herdon et al.

(10) Patent No.: US 6,245,893 B1
(45) Date of Patent: Jun. 12, 2001

(54) RECEPTOR THAT BINDS ANTI-CONVULSANT COMPOUNDS

(75) Inventors: Hugh Jonathan Herdon, Saffron Walden; Jeffrey Clifford Jerman, Aveley; Wai Ngor Chan, Epping, all of (GB)

(73) Assignee: SmithKline Beecham P.L.C., Brentford (GB)

( * ) Notice: Subject to any disclaimer, the term of this patent is extended or adjusted under 35 U.S.C. 154(b) by 0 days.

(21) Appl. No.: 09/413,079

(22) Filed: Oct. 6, 1999

Related U.S. Application Data

(62) Division of application No. 08/849,860, filed as application No. PCT/EP95/04998 on Dec. 11, 1995, now Pat. No. 5,985,334.

(51) Int. Cl.[7] .............................. C07K 1/00; C07K 14/00; C07K 17/00; C07K 16/00; A61K 38/00
(52) U.S. Cl. ............................................. 530/350; 530/300
(58) Field of Search ....................... 530/300, 350

(56) References Cited

U.S. PATENT DOCUMENTS 5,985,334 * 11/1999 Herdon et al. .

FOREIGN PATENT DOCUMENTS

| WO 92/22293 | 12/1992 | (WO) . |
| WO 94/13292 | 6/1994 | (WO) . |
| WO 95/06117 | 3/1995 | (WO) . |

OTHER PUBLICATIONS

Berrie CP, et al. Hydrodynamic properties of muscarinic acetylcholine receptors solubilized from rat forebrain. Br. J. Pharmacol. vol. 82, pp. 839–851, 1984.*

Berrie CP, et al. Purification of the muscarinic acetylcholine receptor from rat forebrain. Biochemical Society Transactions. vol. 13, pp. 1101–1103, 1985.*

Johnson WA, et al., Solubilization and characterization of thyrotropin–releasing hormone receptors from rat brain. Proc. Natl. Acad. Sci. USA, pp. 4227–4231, 1984.*

* cited by examiner

*Primary Examiner*—Gary L. Kunz
*Assistant Examiner*—Robert S. Landsman
(74) *Attorney, Agent, or Firm*—Elizabeth J. Hecht; Edward R. Gimmi; Charles M. Kinzig

(57) ABSTRACT

The claimed invention is substantially purified rat forebrain receptor, wherein said receptor:

a) binds Compound A with a Kd of 40 nM and a $B_{max}$ of 220 pmol/g;

b) binds Compound B with a Kd of 2 nM and a $B_{max}$ of 220 pmol/g protein; and c) has a molecular weight of about 130 kD.

Compounds A and B are known anti-convulsant compounds, such that this receptor will be useful in screening for compounds that have therapeutic activity for the treatment of CNS-related disorders.

2 Claims, No Drawings

RECEPTOR THAT BINDS ANTI-CONVULSANT COMPOUNDS

This is a divisional of application Ser. No. 08/849,860 filed Sep. 26, 1997 now U.S. Pat. No. 5,985,334; which is a 371 of PCT/EP95/04998 filed Dec. 11, 1995; which claims benefit of Foreign Application No. GB 9425502.3 filed Dec. 17, 1994.

The present invention relates to a novel receptor in substantially pure form, to a soluble form of the receptor and it's use as a therapeutic agent, to a method of screening compounds useful in treating disorders by interacting with the receptor, to novel compounds discovered by carrying out the method of screening; to the recombinant receptor and to it's use in such a method of screening; to the preparation of monoclonal and polyclonal antibodies which bind to the receptor; to the use of such antibodies as therapeutic agents and to a method of determining the effectiveness of therapeutic agents which bind to the receptor.

WO 92\22293 (SmithKline Beecham plc) describes a class of compounds which have been shown by behavioural models to possess certain CNS activities, in particular, in the treatment and/or prevention of epilepsy. An example of such a compound described in the above patent application is trans-(+)-6-Acetyl-4S-(4-fluorobenzolamino)-3,4-dihydro-2,2-dimethyl-2H-1-benzopyran-3R-ol. (hereinafter referred to as Compound A).

WO\94\13656, WO\94\13657, WO\94\13292, WO\94\13297, PCT\EP\95\02076, PCT\EP95\02249 and PCT\EP95\02246 all describe other compounds possessing certain CNS activities, in particular PCT\EP95\02076 describes the 'cold' compound of example 4 in the present application i.e. compound B.

The compounds described in the above mentioned patents do not bind at any known receptor and a novel receptor has now been identified to which such compounds bind.

Accordingly the present invention provides a receptor in substantially pure form obtainable from rat forebrain tissue which is characterised in that;
a) compound A binds to it with a Kd of 40 nM for rat forebrain tissue,
b) compound A binds to it with a $B_{max}$ of 220 pmol/g protein for rat forebrain tissue
c) compound B binds to it with a Kd of 2 nM for rat forebrain tissue
d) compound B binds to it with a Bmax of 220 pmol/g protein for rat forebrain tissue;
and homologous receptors from other sources sharing at least 85% homology with the rat forebrain tissue.

Other known anticonvulsant compounds including diazepam, phenytoin, pentobarbitone, valproate, carbamazepine, vigabatrin, lamotrigine, ethosuximide and gabapentin do not bind to the novel receptor.

In addition, the novel receptor can be found in human or rodent neuroblastoma and glioma cell cultures. These can be used without preparation, or can be prepared by the same method as for brain tissue. In human neuroblastoma cell lines e.g. SHSY5Y or AM 32, compound B binds at the novel receptor with a Kd of 2 nM and a Bmax of 150 pmol/g protein.

The novel receptor is isolated in substantially pure form by conventional techniques. For example, an aliquot (for example containing 1 to 10 mg protein/ml) of the tissue containing the novel receptor (for example that described above) is mixed with a radioactively-labelled (for example $^{125}I$) photoaffinity label compound (for example Compound C—see Example 6). Preferably the final concentration of the photoaffinity label compound in the mixture is 0.1 to 1000 pM. The mixture may be suitably incubated for about 1 hour at ambient temperature. The mixture is then exposed to UV light (for example 366 nm from a 6 W lamp) for about 30 min. The tissue is then washed by centrifugation to remove unbound photoaffinity label compound. The photoaffinity labelled receptor can be initially separated from other proteins by gel permeation chromatography (for example with Superose 6) under non-reducing conditions. Protein fractions containing the receptor can then be precipitated with trichloroacetic acid as described by Bensadoun and Weinstein (Bensadoun A., and Weinstein D. (1976) Anal. Biochem. 70, 241–250). The proteins are then further separated by Sodium Dodecyl Sulphate—Polyacrylamide Gel Electrophoresis (SDS-PAGE) under reducing conditions. 6% (w/v) rod gels overlayed with a 5% (w/v) stacking gels, or vertical 10% (w/v), or 4–20% (w/v) gradient, slab gels can be used, based on the method of Laemmli (see Laemmli U.K. (1970) Nature, 227, 680–685). Further purification of the receptor can be achieved by Isoelectric Focussing (IEF) in immobilised pH gradient polyacrylamide gels of material prepared by preparative SDS-PAGE.

The molecular weight of the receptor is in the region of 130 kiloDaltons when analysed by gel electrophoresis (SDS-PAGE).

A second aspect of the invention provides a soluble form of the above receptor.

Soluble forms of said receptor can be prepared according to conventional techniques.

Such soluble forms of said receptor are believed to possess therapeutic utility and therefore the present invention extends to the use of a soluble form of the said receptor as a therapeutic agent.

The present invention also extends to the use of a soluble form of the said receptor in the manufacture of a medicament for treating and/or preventing of anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy; Parkinson's disease, psychosis, migraine and/or cerebral ischaemia.

The present invention also extends to a method of treating and/or preventing anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy; Parkinson's disease, psychosis, migraine and/or cerebral ischaemia, which comprises administering an effective or prophylactic amount of the soluble receptor to a sufferer in need thereof.

The present invention also extends to a pharmaceutical composition for use in the treatment or prevention of anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy Parkinson's disease, psychosis, migraine and/or cerebral ischaemia, which comprises the soluble receptor admixed with pharmaceutically acceptable carriers.

Such pharmaceutical compositions and carriers are well known in the art and can be prepared by conventional techniques.

In a third aspect the present invention provides a method of screening compounds having therapeutic activity associated with binding to the said receptor which comprises; contacting a test compound with a substrate in which the novel receptor is present and measuring the degree of binding.

Substrates in which the novel receptor can be found include but are not limited to brain tissue from rats, humans, marmosets, dogs, cats and mice. Such brain tissue can suitably be homogenised in a buffered aqueous medium such as 5 to 50 mM HEPES, pH 7.4 or Tris/HCl buffer. The homogenised tissue can be washed by centrifugation and resuspension. Subcellular fractions prepared from the tissue can also be used.

Contacting the test compound with a substrate in which the novel receptor is present may be carried out by mixing an aliquot (for example containing 1 to 10 mg protein/ml) of the tissue containing the novel receptor (for example, that described above) with a radioactively-labelled (for example with $^3$H or $^{125}$I) test compound. Preferably the final concentration of the test compound in the mixture is 0.1 to 1000 nM, more preferably 1 to 50 nM.

The mixture may be suitably incubated for about 1 hour at ambient temperature. Unbound test compound is then separated from bound test compound by filtration. This may be carried out using Whatman glass fibre filters preferably of the type GF/B or GF/C. The filters may suitably be washed with ice cold buffered medium (preferably of the type used in the tissue preparation).

The amount of radioactivity bound to the tissue trapped on the filters may be measured by addition of liquid scintillation cocktail to the filters followed by counting in a liquid scintillation counter (for $^3$H) or by direct counting of the filters in a gamma counter (for $^{125}$I).

Alternatively, when using whole cells adherent to a culture plate, unbound test compound can be separated from bound test compound by washing the cells with ice-cold buffered medium, followed by dissolving the cells in sodium hydroxide solution and counting in a liquid scintillation counter or gamma counter as above.

Radio-labelling of the test compound is carried out using conventional techniques.

Alternatively, the binding affinities of non-radio-labelled test compounds may be established by measuring the amount of displacement of a radio-labelled compound which is known to bind to the receptor such as compound (A) and (B) and other compounds mentioned or covered by the aforementioned patents or applications, using conventional techniques.

It should be appreciated that radio-labelled compounds which bind to the receptor and may be displaced using this method of screening are novel and form a further aspect to the present invention.

It may be advantageous to use recombinant receptors in the screening method which may be prepared by conventional techniques.

For example, one means for isolating a novel human receptor coding nucleic acid is to probe a human genomic or cDNA library with a natural or artificially designed probe using art recognised procedures (See for example: "Current Protocols in Molecular Biology", Ausubel, F. M., et al. (eds.) Greene Publishing Assoc. and John Wiley Interscience, New York, 1989,1992). The isolated nucleic acid molecules obtained hereby may be used to obtain complementary copies of genomic DNA, cDNA or RNA from human, mammalian or other animal sources or to screen such sources for related sequences including transcriptional regulatory and control elements defined above as well as other stability, processing, translation and tissue specificity-determining regions from 5' and/or 3' regions relative to the coding sequences.

The proteins of this invention are preferably made by recombinant genetic engineering techniques. The isolated nucleic acids particularly the DNAs can be introduced into expression vectors by operatively linking the DNA to the necessary expression control regions (e.g. regulatory regions) required for gene expression. The vectors can be introduced into the appropriate host cells such as prokaryotic (e.g., bacterial), or eukaryotic (e.g. yeast, insect or mammalian) cells by methods well known in the art (Ausubel et al.,supra). The coding sequences for the desired proteins having been prepared or isolated, can be cloned into a suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), a baculovirus insect cell system,, YCp19 (Saccharomyces). See, generally, "DNA Cloning": Vols. I & XI, Glover et al. ed. IRL Press Oxford (1985) (1987) and; T. Maniatis et al. ("Molecular Cloning" Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the receptors of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of prokaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491. pSV2neo (as described in *J. Mol. Appl. Genet.* 1:327–341) which uses the SV40 late promoter to drive expression in mammalian cells or pCDNA1neo, a vector derived from pCDNA1 (*Mol. Cell Biol.* 7:4125–29) which uses the CMV promoter to drive expression. Both these latter two vectors can be employed for transient or stable (using G418 resistance) expression in mammalian cells. Insect cell expression systems, e.g., Drosophila, are also useful, see for example, PCT applications U.S. 89/05155 and U.S. 91/06838 as well as EP application 88/304093.3.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. In the case, as here, were the protein is localised to the cell surface, whole cells or isolated membranes can be used as an assayable source of the desired gene product. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired receptor The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides is not particularly preferred.

The proteins of the present invention or their fragments comprising at least one epitope can be used to produce antibodies, both polyclonal and monoclonal. If polyclonal antibodies are desired, a selected mammal, (e.g., mouse, rabbit, goat, horse, etc.) is immunised with a receptor of the present invention, or its fragment, or a mutated receptor. Serum from the immunised animal is collected and treated according to known procedures. If serum containing polyclonal antibodies is used, the polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against. Alternatively, genes encoding the monoclonals of interest may be isolated from the hybridomas by PCR techniques known in the art and cloned and expressed in the appropriate vectors. The antibodies of this invention, whether polyclonal or monoclonal have additional utility in that they may be employed reagents in immunoassays, RIA, ELISA, and the like.

In other embodiments cell membrane fractions comprising the receptor or isolated receptors free or immobilised on solid supports may be used to measure binding of the ligand to be tested. When recombinant cells are used for purposes of expression of the receptor it is preferred to use cells with little or no endogenous receptor activity so that binding if any is due to the presence of the expressed receptor of interest. Preferred cells include human embryonic kidney cells, monkey kidney (HEK-293cells), fibroblast (COS) cells, Chinese hamster ovary (CHO) cells, Drosophila or murine L-cells. It is also preferred to employ as a host cell, one in which a receptor responsive second messenger system exists. Well known second messenger systems include but are not limited to increases or decreases in phosphoinositide hydrolysis, adenylate cyclase, guanylate cyclase, or ion channel activity in response to ligand binding to extracellular receptor domains. In a further embodiment a specifically designed indicator of receptor binding can be constructed. For example a fusion protein can be made by fusing the receptor of this invention with a protein domain which is sensitive to receptor ligand binding. Such a domain referred to here as an indicator domain is capable, itself, or in association with accessory molecules, of generating an analytically detectable signal which is indicative of receptor ligand binding.

Alternatively, cell membrane preparations from transfected or transformed cells may be employed. In such a case binding of an analytically detectable ligand is measured. The use of radioactively and non-radioactively labelled ligands is contemplated by this invention. All of the above techniques that are useful for ligand identification are also useful in drug screening and drug development protocols.

A fourth aspect provides novel compounds (hereinafter referred to as compounds of formula (X)) and pharmaceutically acceptable salts, hydrates or solvates thereof identified in the above screening method.

Pharmaceutically acceptable salts, hydrates and saturates thereof may be prepared in conventional manner.

The invention further extends to the use of a compound of formula (X) or a pharmaceutical acceptable salt, hydrate or saturate thereof as a therapeutic agent.

The invention also extends to a method of treating or preventing disorders which comprises administering an effective and/or prophylactic copy amount of a compound of formula (X) or a pharmaceutically acceptable salt, hydrate or solvate thereof to a sufferer in need thereof.

The invention also extends to the use of a compound of formula (X) in the manufacture of a medicament for treating or preventing anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy, Parkinson's disease, psychosis, migraine and/or cerebral ischaemia.

The invention also extends to a pharmaceutical composition for use in treating or preventing anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy, Parkinson's disease, psychosis, migraine and/or cerebral ischaemia, which comprises admixing a compound of formula (X) with a pharmaceutically acceptable carrier.

Such novel compounds identified by the said screening method may be prepared using techniques known in the art of organic chemistry.

A fifth aspect of the present invention provides a monoclonal or polyclonal antibody which binds to the novel receptor.

Such monoclonal and polyclonal anti-bodies may be recognised and prepared by conventional techniques.

The present invention therefore also provides the use of a monoclonal or polyclonal anti-body which binds to the novel receptor as a therapeutic agent.

The inventions further provides the use of a monoclonal or polyclonal antibody which binds to the novel receptor in the manufacture of a medicament for treating and/or preventing anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy; Parkinson's disease, psychosis, migraine and/or cerebral ischaemia.

The invention also provides a method of treating and/or preventing of anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy Parkinson's disease, psychosis, migraine and/or Cerebral ischaemia, which comprises administering an effective and/or prophylactic amount of a monoclonal or polyclonal anti-body which binds to the novel receptor.

The present invention also extends to a pharmaceutical composition for use in treating and/or preventing anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy; Parkinson's disease, psychosis, migraine and/or cerebral ischaemia, which comprises admixing a monoclonal or polyclonal anti-body with a pharmaceutically acceptable carrier.

A sixth aspect of the present invention provides radioactively-labelled compounds which bind to the novel receptor. Such radio-labelled compounds can be prepared by conventional techniques. Particular examples of such compounds are described in the examples. The present invention therefore also provides the use of radio-labelled compounds which binds to the novel receptor as diagnostic tools for detecting changes or abnormalities in the novel receptor. These changes may be present in the disorders associated with binding at the receptor mentioned in the present invention. Such radio-labelled compounds may also be used as research tools to study the properties of the novel receptor. Preferred radio-actively labelled compounds include those given in examples 2 to 5.

The following examples illustrate the present invention.

EXAMPLE 1

Adult male Wistar rats were killed and brains removed by dissection. Whole forebrain tissue was dissected out and homogenised in a buffered aqueous medium. The homogenised tissue was washed by centrifugation and resuspended in the same buffer. After centrifugation the resuspended tissue was either used fresh or stored frozen for periods of up to 3 months or more before use.

Aliquot of tissue prepared as above at a concentration of 1–10 mg protein/ml were mixed with aliquots of [$^3$H]-compound A dissolved in buffered medium (50 nM HEPES, pH7.4). The final concentration of [$^3$H] compound A in the mixture was in the range of 20–50 nM. The mixture was incubated at room temperature for about 1 hour. [$^3$H]-compound A bound to the tissue was then separated from unbound [$^3$H]-compound A by filtration. This filtration was through Whatman glass fibre filters (GF/B or GF/C). The filters were then washed rapidly with ice-cold buffered medium (50 mM HEPES, pH7.4). The amount of radioactivity bound to the tissue trapped on the filters was measured by addition of liquid scintillation cocktail filters followed by counting in a liquid scintillation counter.

In order to determine the amount of "specific" binding of [$^3$H]-compound A (ie. binding specifically to the novel site), parallel assays were carried out as above in which [$^3$H]-compound A and tissue are incubated together in the presence of a high concentration (1–10 $\mu$M) of an unlabelled compound which also binds to the novel site, thus preventing the binding of [$^3$H]-compound A to this site. Unlabelled compound A itself was used, but other compounds which bind to the novel site can also be used. The amount of binding of [$^3$H]-compound A remaining in the presence of this unlabelled compound is defined as "non-specific" binding. This amount is subtracted from the total amount of [$^3$H]-compound A binding (i.e. that present in the absence of unlabelled compound) to obtain the amount of "specific" binding of [$^3$H]-compound A to the novel site.

Estimates of the density of the novel binding site in tissues and its affinity for [$^3$H]-compound A were obtained by incubating tissue together with a range of concentrations of [$^3$H]-compound A. The levels of specific binding (as defined above) at different cocentrations of [$^3$H]-compound A were then used to calculate the dissociation constant ($K_D$) of [$^3$H]-compound A to the novel site and the density ($B_{max}$) of this site in the tissue.

Results

Calculated values for compound A are $K_D$ 40 nM and $B_{max}$ 220 pmol/g protein for rat forebrain tissue.

Using a similar method as described except that the concentration of compound B was approximately 10 fold lower; the calculated values for compound B are KD 2 nM and Bmax 220 pmol/g protein for rat forebrain tissue.

EXAMPLE 2

The synthesis of [carboxyl-$^{14}$C] Compound A and [carboxyl-$^{14}$C] Compound A 1. [Carboxyl-$^{14}$C]4-fluorobenzoic acid To a stirred suspension of potassium[$^{14}$C]cyanide (100 mCi, 60 mCi/mmol$^{-1}$) in anhydrous dimethylformamide was added copper (I) iodide (158 mg, 0.83 mmol) and 4-fluoro-iodobenzene (433 mg, 1.95 mmol). The mixture was heated at reflux, under nitrogen, for 22 hours. The solution was made alkaline by the addition of 5N sodium hydroxide (2 mL) and diluted with water (20 mL). The mixture was thoroughly extracted with diethyl ether, the combined extracts were successively washed with saturated brine (2×30 mL), water (2×30 mL), dried over magnesium sulphate, filtered and the ether distilled off. The residue was dissolved in ethanol (15 mL), potassium hydroxide (1.34 g) in water (8 mL) added, and the resultant solution heated under reflux for 15 hours. The cooled reaction mixture was diluted with water (20 mL), the pH adjusted to 1–2 with 1N hydrochloric acid and the mixture thoroughly extracted with ethyl acetate. The combined extracts were washed with water (1×50 ml), dried over magnesium sulphate, filtered and evaporated to dryness, furnishing [carboxyl-$^{14}$C]4-fluorobenzoic acid (196 mg, 1.38 mmol, 68.4 mCi, 68.4%).

2. [Carboxyl-$^{14}$C]Compound A

[Carboxyl-$^{14}$C]4-fluorobenzoic acid (196 mg, 68.4 mCi, 1.38 mmol), 1-hydroxy-benzotriazole hydrate (191.4 mg, 1.42 mmol) and 1-(3-dimethylaminopropyl)-3-ethylcarbodiimide hydrochloride (265 mg, 1.38 mmol) were dissolved in anhydrous dichloromethane (6 mL). To this was added a solution of (3R,4S)-4-amino-3,4-dihydro-2,2-dimethyl-2H-benzo[b]pyran-3-ol (258 mg, 1.38 mmol, contains 95 w/w methanol)) and triethylamine (0.190 mL) in dichloromethane (2.0 ml). The mixture was stirred at ambient temperature for 19.5 hours and the solvent evaporated in vacuo. The residue was taken up in ethyl acetate (25 mL), washed successively with dilute HCl (2×25 mL), water (25 mL), saturated aqueous sodium bicarbonate (25 mL), water (25 mL), dried over magnesium sulphate, filtered and evaporated to dryness. The crude [carboxyl-$^{14}$C]Compound A was purified by column chromatography (silica 40 g, eluted with ethyl acetate/hexane 1:3 v/v to remove non polar impurities and 100% ethyl acetate to elute [$^{14}$C]Compound A) furnishing [$^{14}$C]Compound A (179.7 mg, 0.50 mmol). A portion (130 mg) of this material was further purified by semi-preparative HPLC (Spherisorb 5W silica 22.5×250 mm column, eluted at 10 ml/min with chloroform/methanol 95:5 v/v) to afford [$^{14}$C]Compound A (107 mg). This batch was allowed to equilibrate over water for 6 hours then thoroughly dried in vacuo. The product had a radiochemical purity of 99.7%, an optical purity >99%, a chemical purity of 95.5% ('as is'), and a specific activity of 59.6 Ci.mmol$^{-1}$. The $^1$H NMR spectrum was consistent with structure and identical to unlabelled compound A as prepared in WO92\22293. Analytical systems are detailed below.

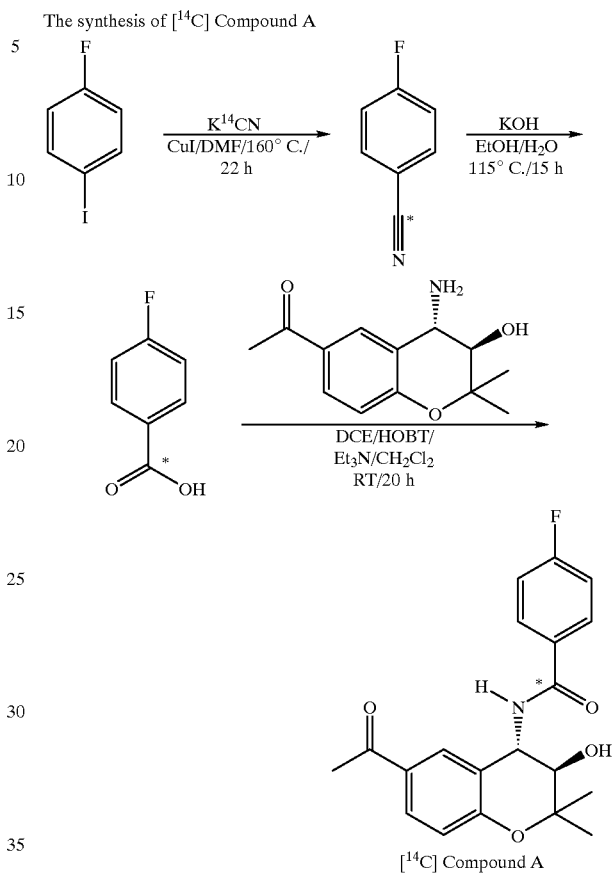

SCHEME 1

The synthesis of [$^{14}$C] Compound A

[$^{14}$C] Compound A

* denotes carbon-14 radiolabel

EXAMPLE 3

The Synthesis of [carboxyl-$^{14}$C] Synthesis of (3S, 4S)-6-acetyl-3,4-dihydro-2,2-dimethyl-4-(3-chloro-4-fluorophenyl[$^{14}$C]carbonylamino)-2H-benzo[b] pyran-3-ol 3-Chloro-4-fluorobenzo[$^{14}$C]nitrile 3-Chloro-4-fluoroiodobenzene (472.8 mg,1.84 mmol), potassium [$^{14}$C] cyanide (100 mCi at specific activity of 60 mCi.mmol$^{-1}$; 1.67 mmol, 108.8 mg) and copper (I) iodide (173.9 mg, 0.91 mmol) were suspended in N-methylpyrrolidinone (4.5 mL).

The mixture was then heated under nitrogen to 150° C., with stirring, for a total of 19.25 hours and allowed to stand at room temperature for 49 hours). Examination by TLC (Silica, eluting ethyl acetate/n-hexane 1:5 v/v) showed that the reaction had proceeded to approximately 73% conversion. The reaction mixture was then partitioned between water (100 mL) and ethyl acetate (100 mL). The organic layer was washed successively with 2% w/v ferric chloride solution (100 mL), water (100 mL), 2% w/v sodium metabisulphite solution (100 mL), water (100 mL) and brine (100 mL). The organic layer was then dried over magnesium sulphate, filtered to remove the desiccant, evaporated to dryness under reduced pressure and the residues subjected to column chromatography on silica (Merck Art. 9385) eluting with ethyl acetate/n-hexane 1:8. Relevant fractions were collected and combined to afford a solution containing approximately 72.7 mCi corresponding to 1.21 mmol, 188 mg; 72.7% yield) of 3-chloro-4-fluorobenzo[$^{14}$C]nitrile.

Synthesis of 3-chloro-4-fluorobenzo[$^{14}$C]carboxylic acid

A solution of 3-chloro-4-fluorobenzo[$^{14}$C]nitrile (36 mCi at specific activity of 60 mCi.mmol-$^{-1}$; 0.6 mmol, 94.5 mg) in ethyl acetate/n-hexane 1:8 v/v (85 mL) was reduced to dryness under reduced pressure. The residues were suspended in concentrated hydrochloric acid (8.0 mL) and heated to 100° C., with stirring, under nitrogen, for 6 hours. At approximately hourly intervals the mixture was agitated to wash back sublimed material into the mixture. The mixture was allowed to cool and stand at room temperature overnight. The mixture was then partitioned between water (30 mL) and ethyl acetate (40 mL). The aqueous layer was extracted again with ethyl acetate (40 mL); the organic layers were combined and extracted into 2M sodium hydroxide solution (40 mL). The organic layer was extracted twice more into 2M sodium hydroxide solution (2×20 mL). The combined alkaline aqueous layers were acidified cautiously to pH 1 by addition of concentrated hydrochloric acid. The aqueous solution was then exctracted twice into ethyl acetate (2×80 mL), the organic layers combined, dried over magnesium sulphate and filtered to remove the desiccant. The desiccant was washed several times with small portions of ethyl acetate (total volume 50 mL) and the washings combined with the filtrate. All solvent was then evaporated under reduced pressure to afford a solid (75 mg, 0.43 mmol, 71.7% yield) of 3-chloro-4-fluorobenzo[$^{14}$C] carboxylic acid.

Synthesis of (3S,4S)-6-acetyl-3,4-dihydro-2,2-dimethyl-4-(3-chloro-4-fluorophenyl[$^{14}$C]carbonylamino)-2H-benzo[b] pyran-3-ol 3-Chloro-4-fluorobenzo[$^{14}$C]carboxylic acid (75 mg, 0.43 mmol) was dissolved in DMF (2.5 mL). To this solution was added hydroxybenztriazole (82.6 mg, 0.61 mmol, 1.42 eq) [dried at room temperature under vacuum for 24 hours] and 1-(3-dimethylaminopropyl)-3-ethylcarbodiimide hydrochloride (113.8 mg, 0.59 mmol, 1.37 eq) [dried at room temperature under vacuum for 24 hours] and the mixture stirred at room temperature for 30 minutes. A solution of (3S,4S)-6-acetyl-3,4-dihydro-2,2-dimethyl-4-amino-2H-benzo[b]pyran-3-ol (150 mg, 0.64 mmol, 1.49 eq) in DMF (2.5 mL) was added and the mixture stirred at room temperature overnight. The mixture was then partitioned between water (50 mL) and ethyl acetate (100 mL); the aqueous layer was extracted again into ethyl acetate (80 mL). The organic layers were combined, washed with water (50 mL), dried over magnesium sulphate and filtered to remove the desiccant. The desiccant was washed on the filter with ethyl acetate (50 mL); the filtrate and the washings were combined and evaporated to dryness under reduced pressure. The residues were subjected to column chromatography on silica eluting with ethyl acetate/n-hexane 1:1 v/v. Relevant column fractions were combined, evaporated to dryness under reduced pressure and the foamy residues thus obtained recrystallised from acetone/n-hexane to afford a white solid product which was dried under vacuum to give 123.5 mg, 0.31 mmol, 72% yield of (3S,4S)-6-acetyl-3,4-dihydro-2,2-dimethyl-4-(3-chloro-4-fluorophenyl[$^{14}$C] carbonylamino)-2H-benzo[b]pyran-3-ol. The product had a radiochemical purity of 98.7%, a chemical purity of 99.4% ('as is'), a chiral purity of 99.9% and a specific activity of 59.4 mCi.mmol-$^{-1}$. The $^1$H NMR spectrum was consistent with the structure and identical to unlabelled compound prepared as described in the abovementioned patents.

EXAMPLE 4

[$^{125}$I]Compound B

Palladium(II) catalysed coupling of unlabelled Compound B with bis(tributyltin) gave the tributylstannane derivative. The target iodine-125 labelled compound, Compound B-[$^{125}$I], was then obtained via radioiododestannylation on a 100 ug portion of the tributyl stannane derivative with 5.0 mCi of sodium iodide-[$^{125}$I] in the presence of 1.0–2.0 ug of chloramine-T as oxidant in 3% acetic acid in ethanol. This procedure gave 3.4–3.9 mCi (68–78% radiochemical yield) of [$^{125}$I]Compound B at a radiochemical purity of at least 99% after HPLC purification (Baker silica gel column, 4.6 mm ID×25 cm, 98:2 hexane/isopropanol, eluted at 1.0 mL/min with UV monitored at 230 nm). Specific activity (derived from measurements of mass and radioactivity concentrations) was determined to be 1775–1800 Ci/mmol.

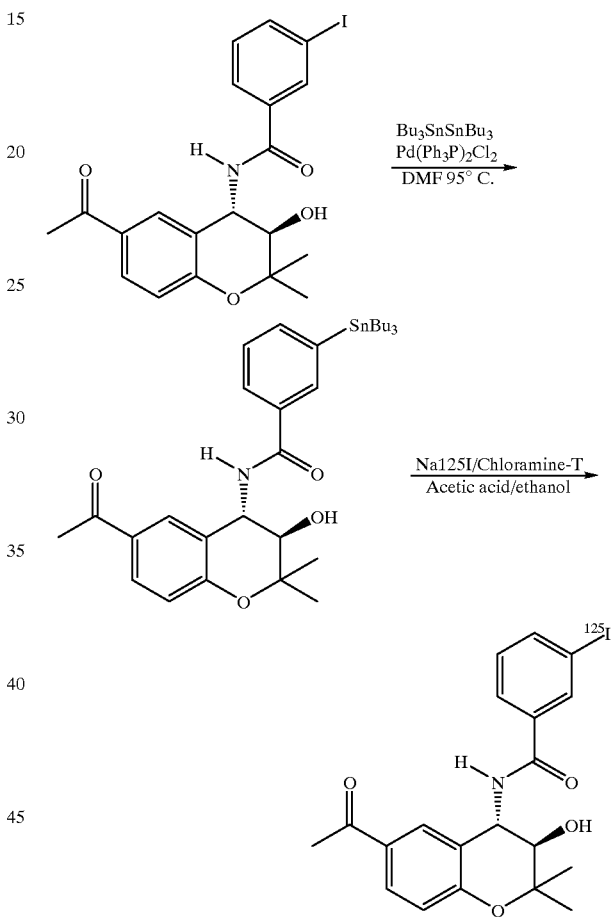

EXAMPLE 5

[$^3$H]Compound A

Compound D (1.0–1.2 mg, 1.9–2.4 umol) was dissolved 1.0 mL of 9:1 (v/v) DMF (Baker)/triethylamine (Aldrich). To this solution was added 1.0–1.2 mg (100 wt %) of 10% palladium on carbon (Aldrich). The reaction mixture was stirred under an atmosphere of 3.6–4.9 Ci of tritium gas for 16–17 h at ambient temperature.

The removal of volatile components by addition of methanol (3×2 mL) followed by vacuum transfer left 108–146 mCi of crude product. Radio-HPLC analysis showed that this material contained 61–66% [$^3$H]Compound A. This material was purified by reverse phase HPLC (Beckman Octyl, 4.6×250 mm column, acetonitrile/water/ trifluoroacetic acid (40:60:0.1), UV detection at 220–240 nm, 1 mL/min flow rate) in four to five injections. The eluate corresponding to product was lyophilized then dissolved in ethanol to provide 24–25 mCi of [$^3$H]Compound A. Analysis gave a specific activity of 21.5–29 Ci/mmol (isotope abundance by chemical ionization-mass spectrometry, NH$_3$ reagent gas) and a radiochemical purity of at least 99% (Ultrasphere ODS 5 um, 4.6×250 mm column, acetonitrile/water/trifluoroacetic acid linear gradient from 34:66:0.1 to 90:10:0.1 over 10 min at 1.0 mL/min, UV detection at 230 nm and radioactivity detection by in-line radioactivity flow scintillation monitor).

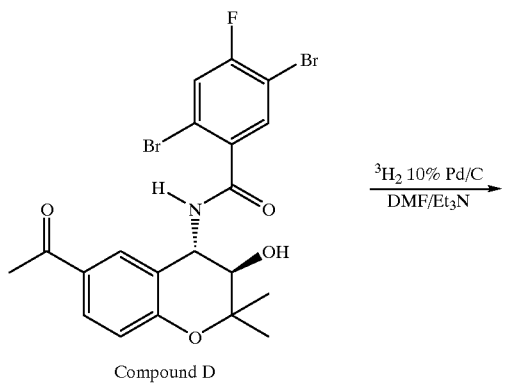

Compound D

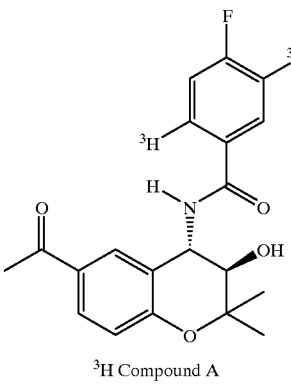

$^3$H Compound A

EXAMPLE 6

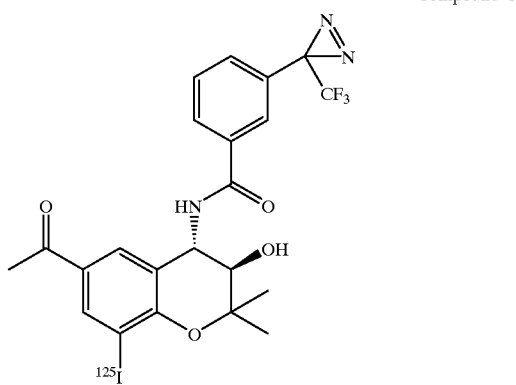

Compound C

The photoaffinity label [$^{125}$I] 6-Acetyl-3,4-dihydro-2,2-dimethyl-8-[$^{125}$I]iodo-4S-[3-{trifluoromethyl-3H-diazirin-3yl}-benzoylamino]-2H-benzo[b]pyran-3R-ol, was prepared by having the radiolabel introduced by ipso substsition of the 8-tributylstannane under standard conditions {Na [$^{125}$I]I (no carrier added)/chloramine-T} and the crude [$^{125}$I] 6-Acetyl-3,4-dihydro-2,2-dimethyl-8-[$^{125}$I]iodo-4S-[3-{trifluoromethyl-3H-diazirin-3yl}-benzoylamino]-2H-benzo[b]pyran-3R-ol, [$^{125}$I]SB-224172 purified by HPLC {Novapak C18 eluted with 0.1% aqueous TFA/acetonitrile (1:1 v/v)}. The stannane was prepared by reaction of 6-acetyl-3,4-dihydro-2,2-dimethyl-8-iodo-4S-amino-2H-benzo[b]pyran-3R-ol with hexabutylditin and dibromopalladium bis(triphenylphosphine) and subsequent condensation with 3-[3-(trifluoromethyl)-3H-diazirin-3-yl]benzoic acid.

Flow Sheet

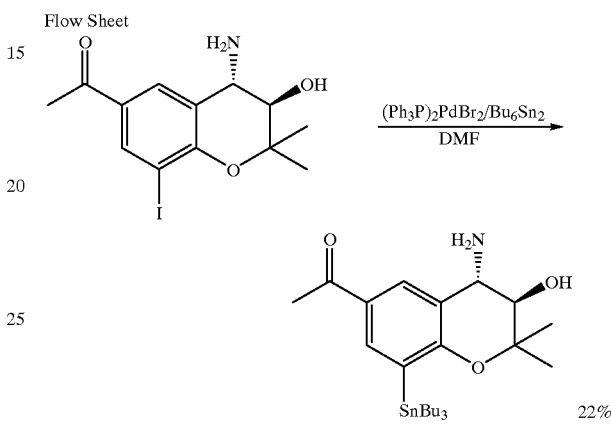

EXAMPLE 7 a) 3-(1,1-Diazirino-2-trifluoroethyl)benzoic acid

To a stirred solution of 3-(1,1-diazirino-2-trifluoroethyl) benzyl alcohol (2.7 g, prepared according to M. Ceruso and G. D. Prestwich, Bioorg and Med Chem Letts, 1994, 4, 2179–2184) in dioxane (10 mL) and 0.2M KOH (63 mL) solution was added KMNO$_4$ (2.45 g) in portions during 2.5 h. The mixture was then filtered through a pad of Celite to remove the excess of MnO$_2$ and the filtrate was extracted with ether. The aqueous layer was acidified with 1M H$_2$SO$_4$ (25 mL) and extracted with ether. The organic layer was washed with water, brine and dried over anh. Na$_2$SO$_4$. Filtration and evaporation in vacuo gave the compound of the description as a light yellow solid (2.45 g).

b) trans-6-Acetyl-4S-(3-(1,1-diazirino-2-trifluoroethyl)-benzoylamino)-3,4-dihydro-2,2-dimethyl-8-iodo-2H-1-benzopyran-3R-ol (Compound C)

To a solution of the diazirinylbenzoic acid of the above description (0.124 g) in dry DMF (2 ml) was added ethyl dimethylaminopropylcarbodiimide hydrochloride (0.095 g) and 1-hydroxybenzotriazole (0.067 g). This solution was stirred at room temperature for 10 min. trans 6-Acetyl-4R-amino-3,4-dihydro-2,2-dimethyl-8-ido-2H-1-benzopyran-3S-ol (0.015 g, as prepared in description 1 and example 8 of PCT/EP/95/02249) was added to the solution and stirring continued for 3 h. The mixture was poured into water and extracted with ethyl acetate. The organic layer was washed with dil HCl, water, saturated NaHCO$_3$ solution and brine and dried over anh. Na$_2$SO$_4$. Filtration and evaporation in vacuo gave a crude solid (0.37 g) which was recrystallised from ethyl acetate:n-hexane to give the compound of example 7 as crystals.

mp 109–100° C.[α]$_D^{25}$+55.3° (MeOH, c=1.1)

What is claimed is:

1. A substantially purified rat forebrain receptor, wherein said receptor:

(a) binds a compound of the formula of Compound A

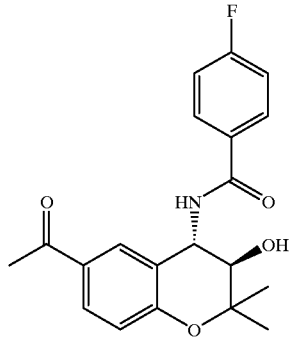

Compound A with a Kd of about 40 nM and with a $B_{MAX}$ of about 220 pmol/g protein;

(b) binds a compound of the formula of Compound B

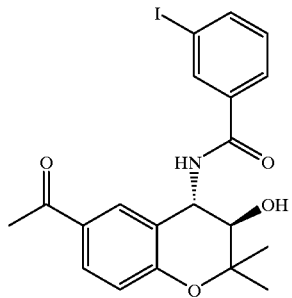

Compound B with a Kd of about 2 nM and a $B_{MAX}$ of about 220 pmol/g; and (c) has a molecular weight of about 130 kD.

2. The receptor as claimed in claim 1, wherein said receptor is in soluble form.

* * * * *